US007718359B2

(12) United States Patent
Guy et al.

(10) Patent No.: US 7,718,359 B2
(45) Date of Patent: May 18, 2010

(54) METHOD OF IMMUNIZATION AGAINST THE 4 SEROTYPES OF DENGUE FEVER

(75) Inventors: Bruno Guy, Lyons (FR); Veronique Barban, Craponne (FR); Remi Forrat, Serezin du Rhone (FR); Jean Lang, Mions (FR)

(73) Assignee: Sanofi Pasteur SA, Lyons (FR)

( * ) Notice: Subject to any disclaimer, the term of this patent is extended or adjusted under 35 U.S.C. 154(b) by 0 days.

(21) Appl. No.: 11/944,311

(22) Filed: Nov. 21, 2007

(65) Prior Publication Data

US 2008/0131460 A1 Jun. 5, 2008

Related U.S. Application Data

(60) Provisional application No. 60/885,077, filed on Jan. 16, 2007.

(30) Foreign Application Priority Data

Dec. 1, 2006 (FR) .................................. 06 55255

(51) Int. Cl.
*C12Q 1/70* (2006.01)
*A61K 39/12* (2006.01)

(52) U.S. Cl. ....................................... 435/5; 424/218.1

(58) Field of Classification Search ....................... None
See application file for complete search history.

(56) References Cited

U.S. PATENT DOCUMENTS

| | | | |
|---|---|---|---|
| 6,638,514 | B1 | 10/2003 | Eckels |
| 2004/0192631 | A1 | 9/2004 | Rong et al. |
| 2004/0259224 | A1 | 12/2004 | Guirakhoo |
| 2008/0014219 | A1 | 1/2008 | Barban et al. |
| 2008/0085288 | A1 | 4/2008 | Guy et al. |

FOREIGN PATENT DOCUMENTS

| | | |
|---|---|---|
| EP | 1159968 | 12/2001 |
| WO | 99/61916 | 12/1999 |
| WO | 00/57910 | 10/2000 |
| WO | 01/21811 | 3/2001 |
| WO | 01/60847 | 8/2001 |
| WO | 01/91790 | 12/2001 |
| WO | 03/101397 | 12/2003 |

OTHER PUBLICATIONS

Whitehead et al. Nature Review Microbiology, Jul. 2007, 5:519-528.*

Shresta et al. J. Virology, Oct. 2006, 80(20):10208-10217.*

Guirakhoo et al., Construction Safety and Immunogenicity non-human primates of a chimeric yellow fever-dengue virus tetravalent vaccine, Journal of Virology-The American Society for Microbiology, Aug. 2001, pp. 7290-7304, vol. 75, No. 10.

Blaney, Joseph, E., Development of a live attenuated dengue virus vaccine using reverse genetics, Viral Immunology, 2006, vol. 19, No. 1, Mary Ann Liebert Inc.

Sabchareon, Arunee et al., Safety and Immunogenecity of tetravalent live-attenuated dengue vaccines in Thai adult volunteers: Role of serotype concentration ratio and multiple doses, American Journal of Tropical Medicine and Hygiene, 2002, pp. 264-272, vol. 66, No. 3.

Guirakhoo et al., Viremia and Immunogenicity in Nonhuman Primates of a Tetravalent Yellow Fever Dengue Chimeric Vaccine Genetic Reconstructions, Dose Adjustment and Antibody Responses against Wild-Type Dengue Virus Isolates, Virology, 2002, vol. 298, No. 1, Academic Press Orlando.

Zhou, H. et al., Sculpting the Immunological Response to Dengue Fever by Polytopic Vaccination, Vaccine, 2005, pp. 2452-2454-2455, vol. 24, No. 14.

Rothman, A.L. et al., Induction of T Lymphocyte Responses to Dengue Virus by a Candidate Tetravalent Live Attenuated Dengue Virus Vaccine, Vaccine, 2001, pp. 4694-4699 + abstract, vol. 19, No. 32.

Bhamarapravati, N. et al., Live Attenuated Tetravalent Dengue Vaccine, Vaccine, 2000, pp. 44-47 + Table 2, vol. 18.

Halstead, S.B. et al., Studies on the Immunization of Monkeys Against Dengue II Protection Following Inoculation of Combinations of Viruses, American Journal of Tropical Medicine & Hygiene, 1973, pp. 375-381, vol. 22, No. 3.

Guirakhoo F., et al., Safety and Afficacy of Chimeric Yellow Fever-Dengue Virus Tetravalent Vaccine Formulations in Nonhuman Primates, Journal of Virology, May 2004, pp. 4761-4775, vol. 78, No. 9.

Halstead, S.B., et al., Protection Derived from Single Sequential Virus Infections, Journal of Tropical Medicine & Hygiene, 1973, pp. 365-374, vol. 22, No. 3.

Final Office Action issued for U.S. Appl. No. 11/866,382, mailed on Jun. 15, 2009.

Final Office Action issued for U.S. Appl. No. 11/776,816, mailed on Jun. 15, 2009.

* cited by examiner

*Primary Examiner*—Stacy B Chen
(74) *Attorney, Agent, or Firm*—McDonnell Boehnen Hulbert & Berghoff LLP

(57) ABSTRACT

The invention relates to a method for inducing protection against the 4 serotypes of dengue fever in a patient, comprising:

(a) the administration of a monovalent vaccine comprising a vaccinal virus of a first serotype of dengue fever, and (b) the administration of a tetravalent vaccine comprising vaccinal viruses of the four serotypes of dengue fever, in which administration (b) is made between at least 30 days and not more than 12 months following the first administration (a).

5 Claims, No Drawings

SEQUENCE LISTING

<160> NUMBER OF SEQ ID NOS: 23

<210> SEQ ID NO 1
<211> LENGTH: 10735
<212> TYPE: DNA
<213> ORGANISM: Dengue virus

<400> SEQUENCE: 1
agttgttagt ctacgtggac cgacaagaac agtttcgaat cggaagcttg cttaacgtag 60
ttctaacagt tttttattag agagcagatc tctgatgatc aaccaacgaa aaaagacggg 120
tcgaccgtct ttcaatatgc tgaaacgcgc gagaaaccgc gtgtcaactg tttcacagtt 180
ggcgaagaga ttctcaaaag gattgctctc aggccaagga cccatgaaat tggtgatggc 240
tttcatagca ttcttaagat ttctagccat acccccaaca gcaggaattt tggctagatg 300
gggctcattc aagaagaatg gagcgattaa agtgttacgg ggtttcaaga gagaaatctc 360
aaacatgcta aacataatga acaggaggaa aagatccgtg accatgctcc ttatgctgct 420
gcccacagcc ctggcgttcc atctgacgac acgagggggga gagccgcata tgatagttag 480
caagcaggaa agaggaaagt cacttttgtt caagacctct gcaggtgtca acatgtgcac 540
cctcattgcg atggatttgg gagagttgtg tgaggacacg atgacctaca aatgcccccg 600
gatcactgag gcggaaccag atgacgttga ctgttggtgc aatgccacgg acacatgggt 660
gacctatgga acgtgctctc aaactggcga acaccgacga gacaaacgtt ccgtcgcatt 720
ggccccacac gtggggcttg gcctagaaac aagagccgaa acgtggatgt cctctgaagg 780
tgcttggaaa cagatacaaa aagtagagac ttgggctctg agacatccag gattcacggt 840
gatagccctt tttctagcac atgccatagg aacatccatc acccagaaag ggatcatttt 900
cattttgctg atgctggtaa caccatctat ggccatgcga tgcgtgggaa taggcaacag 960

-continued

```
agacttcgtg gaaggactgt caggagcaac atgggtggat gtggtactgg agcatggaag   1020
ttgcgtcacc accatggcaa aaaacaaacc aacactggac attgaactct tgaagacgga   1080
ggtcacaaac cctgcagttc tgcgtaaatt gtgcattgaa gctaaaatat caaacaccac   1140
caccgattcg agatgtccaa cacaaggaga agccacactg gtggaagaac aagacgcgaa   1200
ctttgtgtgc cgacgaacgt tcgtggacag aggctggggc aatggctgtg ggctattcgg   1260
aaaaggtagt ctaataacgt gtgccaagtt taagtgtgtg acaaaactag aaggaaagat   1320
agctcaatat gaaaacctaa aatattcagt gatagtcacc gtccacactg gagatcagca   1380
ccaggtggga aatgagacta cagaacatgg aacaactgca accataacac ctcaagctcc   1440
tacgtcggaa atacagctga ccgactacgg aacccttaca ttagattgtt cacctaggac   1500
agggctagat tttaacgaga tggtgttgct gacaatgaaa aagaaatcat ggcttgtcca   1560
caaacagtgg tttctagact taccactgcc ttggacctct ggggctttaa catcccaaga   1620
gacttggaac agacaagatt tactggtcac atttaagaca gctcatgcaa agaagcagga   1680
agtagtcgta ctaggatcac aagaaggagc aatgcacact gcgctgactg gagcgacaga   1740
aatccaaacg tcaggaacga caacaatttt cgcaggacac ctaaaatgca gactaaaaat   1800
ggacaaacta actttaaaag ggatgtcata tgtgatgtgc acaggctcat tcaagttaga   1860
gaaagaagtg gctgagaccc agcatggaac tgttctggtg caggttaaat atgaaggaac   1920
agacgcacca tgcaagattc ccttttcgac ccaagatgag aaaggagcaa cccagaatgg   1980
gagattaata acagccaacc ccatagtcac tgacaaagaa aaaccagtca atattgaggc   2040
agaaccaccc tttggtgaga gctacatcgt ggtaggagca ggtgaaaaag ctttgaaact   2100
aagctggttc aagaaaggaa gcagcatagg gaaaatgttt gaagcaactg cccgaggagc   2160
acgaaggatg gccattctgg gagacaccgc atgggacttc ggttctatag gaggagtgtt   2220
cacgtctatg ggaaaactgg tacaccaggt ttttggaact gcatatggag ttttgtttag   2280
cggagtttct tggaccatga aaataggaat agggattctg ctgacatggc taggattaaa   2340
ttcaaggaac acgtcccttt cggtgatgtg catcgcagtt ggcatggtca cactgtacct   2400
aggagtcatg gttcaggcag attcgggatg tgtaatcaac tggaaaggca gagaacttaa   2460
atgtggaagc ggcatttttg tcactaatga agttcacact tggacagagc aatacaaatt   2520
ccaggctgac tcccccaaga gactatcagc agccattggg aaggcatggg aggagggtgt   2580
gtgtggaatc cgatcagcca ctcgtctcga gaacatcatg tggaaacaaa tatcaaatga   2640
attgaaccac atcctacttg aaaatgacat gaaatttaca gtggtcgtgg gagacgttag   2700
tggaatcttg gcccaaggaa aaaaaatgat taggccacaa cccatggaac acaaatactc   2760
gtggaaaagc tggggaaaag ctaaaatcat aggagcggat gtacagaaca ccaccttcat   2820
catcgacggc ccaaacaccc cagaatgccc tgacaatcaa agagcatgga atatttggga   2880
agtagaggac tatggatttg ggattttcac gacaaacata tggttgaaat tgcgtgactc   2940
ctacacccaa gtatgtgacc accggctgat gtcagctgcc attaaggaca gcaaggcagt   3000
ccatgctgac atggggtact ggatagaaag tgaaaagaac gagacatgga agttggcgag   3060
agcctccttt atagaagtta agacatgcat ctggccaaaa tcccacactc tatggagcaa   3120
tggagttctg gaaagtgaaa tgataattcc aaagatatat ggaggaccaa tatctcagca   3180
caactacaga ccaggatatt tcacacaaac agcagggccg tggcacctag gcaagttgga   3240
actagatttc gatttttgtg aaggtaccac agttgttgtg gatgaacatt gtggaaatcg   3300
aggaccatct ctcagaacca caacagtcac aggaaagata atccatgaat ggtgctgcag   3360
```

-continued

```
atcttgtacg ctaccccccc tacgtttcaa aggggaagac gggtgttggt acggcatgga   3420
aatcagacca gtgaaggaca aggaagagaa cctggtcaag tcaatggtct ctgcagggtc   3480
aggagaagtg gacagctttt cactaggact gctatgcata tcaataatga ttgaagaagt   3540
gatgagatcc agatggagca aaaaaatgct gatgactgga acactggctg tgttcctcct   3600
tcttataatg ggacaattga catggagtga tctgatcagg ttatgtatta tggttggagc   3660
caacgcttca gacaagatgg ggatgggaac aacgtaccta gctttaatgg ccactttcaa   3720
aatgagacca atgttcgccg tcgggctatt atttcgcaga ctaacatcta gagaagttct   3780
tcttcttaca attggcttga gcctggtggc atccgtggag ctaccaagtt ccctagagga   3840
gctgggggat ggacttgcaa taggcatcat gatgttgaaa ttattgactg attttcagtc   3900
acaccagcta tgggctactc tgctatcctt gacatttatt aaaacaactt tttcattgca   3960
ctatgcatgg aagacaatgg ctatggtact gtcaattgta tctctcttcc ctttatgcct   4020
gtccacgacc tctcaaaaaa caacatggct tccggtgctg ttgggatctc ttggatgcaa   4080
accactaccc atgtttctta taacagaaaa caaaatctgg ggaaggaaga gttggcccct   4140
caatgaagga attatggctg ttggaatagt tagtattcta ctaagttcac ttttaaaaaa   4200
tgatgtgccg ctagccggcc cattaatagc tggaggcatg ctaatagcat gttatgtcat   4260
atccggaagc tcagctgatt tatcactgga gaaagcggct gaggtctcct gggaggaaga   4320
agcagaacac tcaggcgcct cacacaacat actagtagag gttcaagatg atggaaccat   4380
gaagataaaa gatgaagaga gagatgacac gctcaccatt ctccttaaag caactctgct   4440
ggcagtctca ggggtgtacc caatgtcaat accagcgacc ctttttgtgt ggtatttttg   4500
gcagaaaaag aaacagagat caggagtgct atgggacaca cccagccccc cagaagtgga   4560
aagagcagtt cttgatgatg gcatctatag aattttgcaa agaggactgt tgggcaggtc   4620
ccaagtagga gtaggagttt tccaagaagg cgtgttccac acaatgtggc acgtcactag   4680
gggagctgtc ctcatgtatc aaggaaaaag gctggaacca agctgggcca gtgtcaaaaa   4740
agacttgatc tcatatggag gaggttggag gtttcaagga tcctggaaca cgggagaaga   4800
agtacaggtg attgctgttg aaccgggaaa aaaccccaaa aatgtacaaa caacgccggg   4860
taccttcaag acccctgaag gcgaagttgg agccatagcc ttagacttta aacctggcac   4920
atctggatct cccatcgtaa acagagaggg aaaaatagta ggtctttatg gaaatggagt   4980
ggtgacaaca agcggaactt acgttagtgc catagctcaa gctaaggcat cacaagaagg   5040
gcctctacca gagattgagg acaaggtgtt taggaaaaga aacttaacaa taatggacct   5100
acatccagga tcgggaaaaa caagaagata ccttccagcc atagtccgtg aggccataaa   5160
aaggaagctg cgcacgctaa tcctagctcc cacaagagtt gtcgcttctg aaatggcaga   5220
ggcactcaag ggagtgccaa taaggtatca gacaacagca gtgaagagtg aacacacagg   5280
aaaggagata gttgacctta tgtgccacgc cactttcacc atgcgcctcc tgtctcccgt   5340
gagagttccc aattataaca tgattatcat ggatgaagca cacttcaccg atccagccag   5400
catagcagcc agagggtaca tctcaacccg agtgggtatg ggtgaagcag ctgcgatctt   5460
tatgacagcc actcccccag gatcggtgga ggcctttcca cagagcaatg caattatcca   5520
agatgaggaa agagacattc ctgagagatc atggaactca ggctatgact ggatcactga   5580
ttttccaggt aaaacagtct ggtttgttcc aagcatcaaa tcaggaaatg acattgccaa   5640
ctgtttaaga aaaaacggga aacgggtgat ccaattgagc agaaaaacct ttgacactga   5700
```

-continued

```
gtaccagaaa acaaaaaaca acgactggga ctatgtcgtc acaacagaca tttccgaaat   5760
gggagcaaat ttccgggccg acagggtaat agacccaagg cggtgtctga aaccggtaat   5820
actaaaagat ggtccagagc gcgtcattct agccggaccg atgccagtga ctgtggccag   5880
tgccgcccag aggagaggaa gaattggaag gaaccaaaac aaggaaggtg atcagtatat   5940
ttacatggga cagcctttaa aaaatgatga ggaccacgct cattggacag aagcaaagat   6000
gctccttgac aatataaaca caccagaagg gattatccca gccctctttg agccggagag   6060
agaaaagagt gcagctatag acggggaata cagactgcgg ggtgaagcaa ggaaaacgtt   6120
cgtggagctc atgagaagag gggatctacc agtctggcta tcctacaaag ttgcctcaga   6180
aggcttccag tactccgaca gaaggtggtg cttcgatggg gaaaggaaca accaggtgtt   6240
ggaggagaac atggacgtgg agatctggac aaaagaagga gaaagaaaga aactacgacc   6300
tcgctggttg gacgccagaa catactctga cccactggct ctgcgcgagt ttaaagagtt   6360
tgcagcagga agaagaagcg tctcaggtga cctaatatta gaaataggga aacttccaca   6420
acatttgacg caaagggccc agaatgcttt ggacaacttg gtcatgttgc acaattccga   6480
acaaggagga aaagcctata gacatgctat ggaagaactg ccagacacaa tagaaacgtt   6540
gatgctccta gccttgatag ctgtgttgac tggtggagtg acgctgttct tcctatcagg   6600
aagaggtcta ggaaaaacat ctatcggctt actctgcgtg atggcctcaa gcgcactgtt   6660
atggatggcc agtgtggagc cccattggat agcggcctcc atcatactgg agttctttct   6720
gatggtactg cttattccag agccagacag acagcgcact ccacaggaca accagctagc   6780
atatgtggtg ataggtctgt tattcgtgat attgacagtg gcagccaatg agatgggatt   6840
attggaaacc acaaagaaag acctggggat tggccatgta gctgctgaaa accaccacca   6900
tgctacaatg ctggacgtag acctacatcc agcttcagcc tggaccctct atgcagtggc   6960
cacaacaatc atcactccta tgatgagaca cacaattgaa aacacaacgg caaatatttc   7020
cctgacagcc atcgcaaacc aagcagctat attgatggga cttgacaagg gatggccaat   7080
atcgaagatg gacataggag ttccacttct cgccttgggg tgctattccc aagtgaatcc   7140
gctgacactg atagcggcag tattgatgct agtagctcat tacgccataa ttggacctgg   7200
actgcaagca aaagctacta gagaagctca aaaaagaaca gcggctggaa taatgaaaaa   7260
tccaactgtc gacgggattg ttgcaataga cttagatccc gtggtttacg atgcaaaatt   7320
tgaaaaacag ctaggccaaa taatgttgtt gatactttgc acatcacaga ttcttttgat   7380
gcggactaca tgggccttgt gtgaatccat cacattggct actggacctc tgaccactct   7440
ttgggaggga tctccaggaa aattctggaa caccacaata gcggtatcca tggcaaacat   7500
tttcaggggg agttatctag caggagcagg tctggccttc tcattaatga aatctctagg   7560
aggaggtagg agaggcacgg gagcccaagg ggaaacactg ggagaaaaat ggaaaagaca   7620
actaaaccaa ctgagcaagt cagaattcaa tacttacaag aggagtggga ttatggaggt   7680
ggatagatcc gaagccaaag agggactgaa aagaggagaa acaaccaaac acgcagtatc   7740
gagaggaacg gccaaactga ggtggttcgt ggagaggaac cttgtgaaac cagaagggaa   7800
agtcatagac ctcggttgtg gaagaggtgg ctggtcatat tattgcgctg ggctgaagaa   7860
agtcacagaa gtgaaaggat acacaaaagg aggacctgga catgaggaac caatcccaat   7920
ggcgacctat ggatggaacc tagtaaggct gcactccgga aaagatgtat tttttatacc   7980
acctgagaaa tgtgacaccc ttttgtgtga tattggtgag tcctctccga acccaactat   8040
agaggaagga agaacgttac gtgttctgaa aatggtggaa ccatggctca gaggaaacca   8100
```

-continued

```
attttgcata aaaattctaa atccctatat gccgagcgtg gtagaaactc tggaacaaat   8160
gcaaagaaaa catggaggaa tgctagtgcg aaacccactc tcaagaaatt ccacccatga   8220
aatgtactgg gtttcatgtg gaacaggaaa cattgtgtca gcagtaaaca tgacatctag   8280
aatgttgcta aatcggttca caatggctca caggaagcca acatatgaaa gagacgtgga   8340
cttaggcgct ggaacaagac atgtggcagt agaaccagag gtagccaacc tagatatcat   8400
tggccagagg atagagaata taaaaaatga acataagtca acatggcatt atgatgagga   8460
caatccatac aaaacatggg cctatcatgg atcatatgag gttaagccat caggatcggc   8520
ctcatccatg gtcaatggcg tggtgagatt gctcaccaaa ccatgggatg ttatccccat   8580
ggtcacacaa atagccatga ctgataccac accctttgga caacagaggg tgtttaaaga   8640
gaaagttgac acgcgcacac caaaagcaaa acgtggcaca gcacaaatta tggaagtgac   8700
agccaggtgg ttatggggtt tcctttctag aaacaaaaaa cccagaattt gcacaagaga   8760
ggagtttaca agaaaagtta ggtcaaacgc agctattgga gcagtgttcg ttgatgaaaa   8820
tcaatggaac tcggcaaaag aagcagtgga agacgaacgg ttctgggaac ttgtccacag   8880
agagagggag cttcataaac aggggaaatg tgccacgtgt gtctacaata tgatggggaa   8940
gagagagaaa aaattaggag agttcggaaa ggcaaaagga agtcgtgcaa tatggtacat   9000
gtggttggga gcacgcttcc tagagtttga agcccttggt ttcatgaatg aagatcactg   9060
gttcagtaga gagaattcac tcagtggagt ggaaggagaa ggactccaca aacttggata   9120
catactcaga gacatatcaa ggattccagg ggggaacatg tatgcagatg acacagccgg   9180
atgggacaca agaataacag aggatgatct ccagaatgag gctaaaatca ctgacatcat   9240
ggagcccgaa catgccctgc tggctacgtc aatctttaag ctgacctacc aaaataaggt   9300
ggtaagggtg cagagaccag caaaaaatgg aaccgtgatg gatgttatat ccagacgtga   9360
ccagagaggc agtggacagg ttggaactta tggcttaaac actttcacca acatggaggc   9420
ccaactgata agacaaatgg agtctgaggg aatcttttta cccagcgaat tggaaacccc   9480
aaatctagcc ggaagagttc tcgactggtt ggaaaaatat ggtgtcgaaa ggctgaaaag   9540
aatggcaatc agcggagatg actgtgtggt gaaaccaatt gatgacaggt tcgcaacagc   9600
cttaacagct ttgaatgaca tgggaaaagt aagaaaagac ataccacaat gggaaccttc   9660
aaaaggatgg aatgattggc aacaagtgcc tttctgttca caccacttcc accagctaat   9720
tatgaaggat gggagggaga tagtggtgcc atgccgcaac caagatgaac ttgtggggag   9780
ggccagagta tcacaaggcg ccggatggag cctgagagaa accgcatgcc taggcaagtc   9840
atatgcacaa atgtggcagc tgatgtattt ccacaggaga gacctgagac tggcggctaa   9900
cgctatttgt tcagccgttc cagttgattg ggtcccaacc agccgcacca cctggtcgat   9960
ccatgcccat caccaatgga tgacaacaga agacatgtta tcagtatgga atagggtctg  10020
gatagaggaa aacccatgga tggaggataa gactcatgtg tccagttggg aagaagttcc  10080
atacctagga aagagggaag atcagtggtg tggatccctg ataggcttaa cagcaagggc  10140
cacctgggcc actaatatac aagtggccat aaaccaagtg agaaggctca ttgggaatga  10200
gaattatcta gattacatga catcaatgaa gagattcaag aatgagagtg atcccgaagg  10260
ggcactctgg taagtcaaca cattcacaaa ataaaggaaa ataaaaaatc aaatgaggca  10320
agaagtcagg ccagattaag ccatagtacg gtaagagcta tgctgcctgt gagccccgtc  10380
caaggacgta aaatgaagtc aggccgaaag ccacggtttg agcaagccgt gctgcctgtg  10440
```

-continued

```
gctccatcgt ggggatgtaa aaacccggga ggctgcaacc catggaagct gtacgcatgg  10500

ggtagcagac tagtggttag aggagacccc tcccaagaca caacgcagca gcggggccca  10560

acaccagggg aagctgtacc ctggtggtaa ggactagagg ttagaggaga ccccccgcgt  10620

aacaataaac agcatattga cgctgggaga gaccagagat cctgctgtct ctacagcatc  10680

attccaggca cagaacgcca gaaaatggaa tggtgctgtt gaatcaacag gttct       10735
```

<210> SEQ ID NO 2
<211> LENGTH: 10723
<212> TYPE: DNA
<213> ORGANISM: Dengue virus

<400> SEQUENCE: 2

```
agttgttagt ctacgtggac cgacaaagac agattctttg agggagctaa gctcaatgta     60

gttctaacag tttttaatt agagagcaga tctctgatga ataaccaacg gaaaaaggcg    120

aaaaacacgc ctttcaatat gctgaaacgc gagagaaacc gcgtgtcgac tgtgcaacag    180

ctgacaaaga gattctcact tggaatgctg cagggacgag gaccattaaa actgttcatg    240

gccctggtgg cgttccttcg tttcctaaca atcccaccaa cagcagggat attgaagaga    300

tggggaacaa ttaaaaaatc aaaagctatt aatgttttga gagggttcag gaaagagatt    360

ggaaggatgc tgaacatctt gaataggaga cgcagatctg caggcatgat cattatgctg    420

attccaacag tgatggcgtt ccatttaacc acacgtaacg gagaaccaca catgatcgtc    480

agcagacaag agaaagggaa aagtcttctg tttaaaacag aggttggcgt gaacatgtgt    540

accctcatgg ccatggacct tggtgaattg tgtgaagaca caatcacgta caagtgtccc    600

cttctcaggc agaatgagcc agaagacata gactgttggt gcaactctac gtccacgtgg    660

gtaacttatg ggacgtgtac caccatggga gaacatagaa gagaaaaaag atcagtggca    720

ctcgttccac atgtgcgaat gggactggag acacgaactg aaacatggat gtcatcagaa    780

ggggcctgga aacatgtcca gagaattgaa acttggatct tgagacatcc aggcttcacc    840

atgatggcag caatcctggc atacaccata ggaacgacac atttccaaag agccctgatt    900

ttcatcttac tgacagctgt cactccttca atgacaatgc gttgcatagg aatgtcaaat    960

agagactttg tggaaggggt ttcaggagga agctgggttg acatagtctt agaacatgga   1020

agctgtgtga cgacgatggc aaaaaaacaaa ccaacattgg attttgaact gataaaaaca   1080

gaagccaaac agcctgccac cctaaggaag tactgtatag aggcaaagct aaccaacaca   1140

acaacagaat ctcgctgccc aacacaaggg gaacccagcc taaatgaaga gcaggacaaa   1200

aggttcgtct gcaaacactc catggtagac agaggatggg gaaatggatg tggactattt   1260

ggaaagggag gcattgtgac ctgtgctatg ttcagatgca aaaagaacat ggaaggaaaa   1320

gttgtgcaac cagaaaactt ggaatacacc attgtgataa cacctcactc aggggaagag   1380

catgcagtcg gaaatgacac aggaaaacat ggcaaggaaa tcaaaataac accacagagt   1440

tccatcacag aagcagaatt gacaggttat ggcactgtca caatggagtg ctctccaaga   1500

acgggcctcg acttcaatga gatggtgttg ctgcagatgg aaaataaagc ttggctggtg   1560

cacaggcaat ggttcctaga cctgccgtta ccatggttgc ccggagcgga cacacaagag   1620

tcaaattgga tacagaagga gacattggtc actttcaaaa atccccatgc gaagaaacag   1680

gatgttgttg ttttaggatc ccaagaaggg gccatgcaca cagcacttac aggggccaca   1740

gaaatccaaa tgtcatcagg aaacttactc ttcacaggac atctcaagtg caggctgaga   1800

atggacaagc tacagctcaa aggaatgtca tactctatgt gcacaggaaa gtttaaagtt   1860
```

-continued

```
gtgaaggaaa tagcagaaac acaacatgga acaatagtta tcagagtgca atatgaaggg   1920
gacggctctc catgcaagat cccttttgag ataatggatt tggaaaaaag acatgtctta   1980
ggtcgcctga ttacagtcaa cccaattgtg acagaaaaag atagcccagt caacatagaa   2040
gcagaacctc catttggaga cagctacatc atcataggag tagagccggg acaactgaag   2100
ctcaactggt ttaagaaagg aagttctatc ggccaaatgt ttgagacaac aatgaggggg   2160
gcgaagagaa tggccatttt aggtgacaca gcctgggatt ttggatcctt gggaggagtg   2220
tttacatcta taggaaaggc tctccaccaa gtctttggag caatctatgg agctgccttc   2280
agtggggttt catggactat gaaaatcctc ataggagtca ttatcacatg gataggaatg   2340
aattcacgca gcacctcact gtctgtgaca ctagtattgg tgggaattgt gacactgtat   2400
ttgggagtca tggtgcaggc cgatagtggt tgcgttgtga gctggaaaaa caaagaactg   2460
aaatgtggca gtgggatttt catcacagac aacgtgcaca catggacaga acaatacaaa   2520
ttccaaccag aatccccttc aaaactagct tcagctatcc agaaagccca tgaagaggac   2580
atttgtggaa tccgctcagt aacaagactg gagaatctga tgtggaaaca aataacacca   2640
gaattgaatc acattctatc agaaaatgag gtgaagttaa ctattatgac aggagacatc   2700
aaaggaatca tgcaggcagg aaaacgatct ctgcggcctc agcccactga gctgaagtat   2760
tcatggaaaa catggggcaa agcaaaaatg ctctctacag agtctcataa ccagaccttt   2820
ctcattgatg gccccgaaac agcagaatgc cccaacacaa atagagcttg gaattcgttg   2880
gaagttgaag actatggctt tggagtattc accaccaata tatggctaaa attgaaagaa   2940
aaacaggatg tattctgcga ctcaaaactc atgtcagcgg ccataaaaga caacagagcc   3000
gtccatgccg atatgggtta ttggatagaa agtgcactca atgacacatg gaagatagag   3060
aaagcctctt tcattgaagt taaaaactgc cactggccaa aatcacacac cctctggagc   3120
aatggagtgc tagaaagtga gatgataatt ccaaagaatc tcgctggacc agtgtctcaa   3180
cacaactata gaccaggcta ccatacacaa ataacaggac catggcatct aggtaagctt   3240
gagatggact ttgatttctg tgatggaaca acagtggtag tgactgagga ctgcggaaat   3300
agaggaccct ctttgagaac aaccactgcc tctggaaaac tcataacaga atggtgctgc   3360
cgatcttgca cattaccacc gctaagatac agaggtgagg atgggtgctg gtacgggatg   3420
gaaatcagac cattgaagga gaaagaagag aatttggtca actccttggt cacagctgga   3480
catgggcagg tcgacaactt ttcactagga gtcttgggaa tggcattgtt cctggaggaa   3540
atgcttagga cccgagtagg aacgaaacat gcaatactac tagttgcagt ttcttttgtg   3600
acattgatca cagggaacat gtcctttaga gacctgggaa gagtgatggt tatggtaggc   3660
gccactatga cggatgacat aggtatgggc gtgacttatc ttgccctact agcagccttc   3720
aaagtcagac caacttttgc agctggacta ctcttgagaa agctgacctc caaggaattg   3780
atgatgacta ctataggaat tgtactcctc tcccagagca ccataccaga gaccattctt   3840
gagttgactg atgcgttagc cttaggcatg atggtcctca aaatggtgag aaatatggaa   3900
aagtatcaat tggcagtgac tatcatggct atcttgtgcg tcccaaacgc agtgatatta   3960
caaaacgcat ggaaagtgag ttgcacaata ttggcagtgg tgtccgtttc cccactgttc   4020
ttaacatcct cacagcaaaa aacagattgg ataccattag cattgacgat caaaggtctc   4080
aatccaacag ctatttttct aacaaccctc tcaagaacca gcaagaaaag gagctggcca   4140
ttaaatgagg ctatcatggc agtcgggatg gtgagcattt tagccagttc tctcctaaaa   4200
```

-continued

```
aatgatattc ccatgacagg accattagtg gctggagggc tcctcactgt gtgctacgtg   4260
ctcactggac gatcggccga tttggaactg gagagagcag ccgatgtcaa atgggaagac   4320
caggcagaga tatcaggaag cagtccaatc ctgtcaataa caatatcaga agatggtagc   4380
atgtcgataa aaaatgaaga ggaagaacaa acactgacca tactcattag aacaggattg   4440
ctggtgatct caggactttt tcctgtatca ataccaatca cggcagcagc atggtacctg   4500
tgggaagtga agaaacaacg ggccggagta ttgtgggatg ttccttcacc cccacccatg   4560
ggaaaggctg aactggaaga tggagcctat agaattaagc aaaaagggat tcttggatat   4620
tcccagatcg gagccggagt ttacaaagaa ggaacattcc atacaatgtg gcatgtcaca   4680
cgtggcgctg ttctaatgca taaaggaaag aggattgaac caacatgggc ggacgtcaag   4740
aaagacctaa tatcatatgg aggaggctgg aagttagaag gagaatggaa ggaaggagaa   4800
gaagtccagg tattggcact ggagcctgga aaaaatccaa gagccgtcca aacgaaacct   4860
ggtcttttca aaaccaacgc cggaacaata ggtgctgtat ctctggactt ttctcctgga   4920
acgtcaggat ctccaattat cgacaaaaaa ggaaaagttg tgggtcttta tggtaatggt   4980
gttgttacaa ggagtggagc atatgtgagt gctatagccc agactgaaaa aagcattgaa   5040
gacaacccag agatcgaaga tcacattttc cgaaagagaa gactgaccat catggacctc   5100
cacccaggag cgggaaagac gaagagatac cttccggcca tagtcagaga agctataaaa   5160
cggggtttga gaacattaat cttggccccc actagagttg tggcagctga aatggaggaa   5220
gcccttagag gacttccaat aagataccag accccagcca tcagagctga gcacaccggg   5280
cgggagattg tggacctaat gtgtcatgcc acatttacca tgaggctgct atcaccagtt   5340
agagtgccaa actacaacct gattatcatg gacgaagccc atttcacaga cccagcaagt   5400
atagcagcta gaggatacat ctcaactcga gtggagatgg gtgaggcagc tgggattttt   5460
atgacagcca ctcccccggg aagcagagac ccatttcctc agagcaatgc accaatcata   5520
gatgaagaaa gagaaatccc tgaacgctcg tggaattccg gacatgaatg ggtcacggat   5580
tttaaaggga agactgtttg gttcgttcca agtataaaag caggaaatga tatagcagct   5640
tgcctgagga aaaatggaaa gaaagtgata caactcagta ggaagacctt tgattctgag   5700
tatgtcaaga ctagaaccaa tgattgggac ttcgtggtta caactgacat ttcagaaatg   5760
ggtgccaatt tcaaggctga gagggttata gaccccagac gctgcatgaa accagtcata   5820
ctaacagatg gtgaagagcg ggtgattctg gcaggaccta tgccagtgac ccactctagt   5880
gcagcacaaa gaagagggag aataggaaga aatccaaaaa atgagaatga ccagtacata   5940
tacatggggg aacctctgga aaatgatgaa gactgtgcac actggaaaga agctaaaatg   6000
ctcctagata acatcaacac gccagaagga atcattccta gcatgttcga accagagcgt   6060
gaaaaggtgg atgccattga tggcgaatac cgcttgagag gagaagcaag gaaaaccttt   6120
gtagacttaa tgagaagagg agacctacca gtctggttgg cctacagagt ggcagctgaa   6180
ggcatcaact acgcagacag aaggtggtgt tttgatggag tcaagaacaa ccaaatccta   6240
gaagaaaacg tggaagttga aatctggaca aaagaagggg aaaggaagaa attgaaaccc   6300
agatggttgg atgctaggat ctattctgac ccactggcgc taaaagaatt taaggaattt   6360
gcagccggaa gaaagtctct gaccctgaac ctaatcacag aaatgggtag gctcccaacc   6420
ttcatgactc agaaggcaag agacgcactg gacaacttag cagtgctgca cacggctgag   6480
gcaggtggaa gggcgtacaa ccatgctctc agtgaactgc cggagaccct ggagacattg   6540
cttttactga cacttctggc tacagtcacg ggagggatct tttattcttt gatgagcgca   6600
```

-continued

```
aggggcatag ggaagatgac cctgggaatg tgctgcataa tcacggctag catcctccta   6660
tggtacgcac aaatacagcc acactggata gcagcttcaa taatactgga gtttttctc    6720
atagttttgc ttattccaga acctgaaaaa cagagaacac cccaagacaa ccaactgacc   6780
tacgttgtca tagccatcct cacagtggtg gccgcaacca tggcaaacga gatgggtttc   6840
ctagaaaaaa cgaagaaaga tctcggattg ggaagcattg caacccagca acccgagagc   6900
aacatcctgg acatagatct acgtcctgca tcagcatgga cgctgtatgc cgtggccaca   6960
acatttgtta caccaatgtt gagacatagc attgaaaatt cctcagtgaa tgtgtcccta   7020
acagctatag ccaaccaagc cacagtgtta atgggtctcg ggaaaggatg gccattgtca   7080
aagatggaca tcggagttcc ccttctcgcc attggatgct actcacaagt caaccccata   7140
actctcacag cagctctttt cttattggta gcacattatg ccatcatagg gccaggactc   7200
caagcaaaag caaccagaga agctcagaaa agagcagcgg cgggcatcat gaaaaaccca   7260
actgtcgatg gaataacagt gattgaccta gatccaatac cttatgatcc aaagtttgaa   7320
aagcagttgg gacaagtaat gctcctagtc ctctgcgtga ctcaagtatt gatgatgagg   7380
actacatggg ctctgtgtga ggctttaacc ttagctaccg ggcccatctc cacattgtgg   7440
gaaggaaatc cagggaggtt ttggaacact accattgcgg tgtcaatggc taacattttt   7500
agagggagtt acttggccgg agctggactt ctcttttcta ttatgaagaa cacaaccaac   7560
acaagaaggg gaactggcaa cataggagag acgcttggag agaaatggaa aagccgattg   7620
aacgcattgg gaaaaagtga attccagatc tacaagaaaa gtggaatcca ggaagtggat   7680
agaaccttag caaaagaagg cattaaaaga ggagaaacgg accatcacgc tgtgtcgcga   7740
ggctcagcaa aactgagatg gttcgttgag agaaacatgg tcacaccaga agggaaagta   7800
gtggacctcg gttgtggcag aggaggctgg tcatactatt gtggaggact aaagaatgta   7860
agagaagtca aaggcctaac aaaaggagga ccaggacacg aagaacccat ccccatgtca   7920
acatatgggt ggaatctagt gcgtcttcaa agtggagttg acgttttctt catcccgcca   7980
gaaaagtgtg acacattatt gtgtgacata ggggagtcat caccaaatcc cacagtggaa   8040
gcaggacgaa cactcagagt ccttaactta gtagaaaatt ggttgaacaa caacactcaa   8100
ttttgcataa aggttctcaa cccatatatg ccctcagtca tagaaaaaat ggaagcacta   8160
caaaggaaat atggaggagc cttagtgagg aatccactct cacgaaactc cacacatgag   8220
atgtactggg tatccaatgc ttccgggaac atagtgtcat cagtgaacat gatttcaagg   8280
atgttgatca acagatttac aatgagatac aagaaagcca cttacgagcc ggatgttgac   8340
ctcggaagcg gaacccgtaa catcgggatt gaaagtgaga taccaaacct agatataatt   8400
gggaaaagaa tagaaaaaat aaagcaagag catgaaacat catggcacta tgaccaagac   8460
cacccataca aaacgtgggc ataccatggt agctatgaaa caaaacagac tggatcagca   8520
tcatccatgg tcaacggagt ggtcaggctg ctgacaaaac cttgggacgt tgtccccatg   8580
gtgacacaga tggcaatgac agacacgact ccatttggac aacagcgcgt ttttaaagag   8640
aaagtggaca cgagaaccca agaaccgaaa gaaggcacga agaaactaat gaaaataaca   8700
gcagagtggc tttggaaaga attagggaag aaaaagacac ccaggatgtg caccagagaa   8760
gaattcacaa gaaaggtgag aagcaatgca gccttggggg ccatattcac tgatgagaac   8820
aagtggaagt cggcacgtga ggctgttgaa gatagtaggt tttgggagct ggttgacaag   8880
gaaaggaatc tccatcttga aggaaagtgt gaaacatgtg tgtacaacat gatgggaaaa   8940
```

-continued agagagaaga agctagggga attcggcaag gcaaaaggca gcagagccat atggtacatg 9000
tggcttggag cacgcttctt agagtttgaa gccctaggat tcttaaatga agatcactgg 9060
ttctccagag agaactccct gagtggagtg gaaggagaag ggctgcacaa gctaggttac 9120
attctaagag acgtgagcaa gaaagaggga ggagcaatgt atgccgatga caccgcagga 9180
tgggatacaa aaatcacact agaagaccta aaaaatgaag agatggtaac aaaccacatg 9240
gaaggagaac acaagaaact agccgaggcc attttcaaac taacgtacca aaacaaggtg 9300
gtgcgtgtgc aaagaccaac accaagaggc acagtaatgg acatcatatc gagaagagac 9360
caaagaggta gtggacaagt tggcacctat ggactcaata ctttcaccaa tatggaagcc 9420
caactaatca gacagatgga gggagaagga gtctttaaaa gcattcagca cctaacaatc 9480
acagaagaaa tcgctgtgca aaactggtta gcaagagtgg ggcgcgaaag gttatcaaga 9540
atggccatca gtggagatga ttgtgttgtg aaacctttag atgacaggtt cgcaagcgct 9600
ttaacagctc taaatgacat gggaaagatt aggaaagaca tacaacaatg ggaaccttca 9660
agaggatgga atgattggac acaagtgccc ttctgttcac accatttcca tgagttaatc 9720
atgaaagacg gtcgcgtact cgttgttcca tgtagaaacc aagatgaact gattggcaga 9780
gcccgaatct cccaaggagc agggtggtct ttgcgggaga cggcctgttt ggggaagtct 9840
tacgcccaaa tgtggagctt gatgtacttc cacagacgcg acctcaggct ggcggcaaat 9900
gctatttgct cggcagtacc atcacattgg gttccaacaa gtcgaacaac ctggtccata 9960
catgctaaac atgaatggat gacaacggaa gacatgctga cagtctggaa cagggtgtgg 10020
attcaagaaa acccatggat ggaagacaaa actccagtgg aaacatggga ggaaatccca 10080
tacttgggga aaagagaaga ccaatggtgc ggctcattga ttgggttaac aagcagggcc 10140
acctgggcaa agaacatcca agcagcaata aatcaagtta gatcccttat aggcaatgaa 10200
gaatacacag attacatgcc atccatgaaa agattcagaa gagaagagga agaagcagga 10260
gttctgtggt agaaagcaaa actaacatga aacaaggcta gaagtcaggt cggattaagc 10320
catagtacgg aaaaaactat gctacctgtg agccccgtcc aaggacgtta aaagaagtca 10380
ggccatcata aatgccatag cttgagtaaa ctatgcagcc tgtagctcca cctgagaagg 10440
tgtaaaaaat ccgggaggcc acaaaccatg gaagctgtac gcatggcgta gtggactagc 10500
ggttagggga gacccctccc ttacaaatcg cagcaacaat gggggcccaa ggcgagatga 10560
agctgtagtc tcgctggaag gactagaggt tagaggagac ccccccgaaa caaaaaacag 10620
catattgacg ctgggaaaga ccagagatcc tgctgtctcc tcagcatcat tccaggcaca 10680
gaacgccaga aaatggaatg gtgctgttga atcaacaggt tct 10723

<210> SEQ ID NO 3
<211> LENGTH: 23
<212> TYPE: DNA
<213> ORGANISM: Artificial
<220> FEATURE:
<223> OTHER INFORMATION: Synthetic

<400> SEQUENCE: 3
gcacggatgt aacagactga aga 23

<210> SEQ ID NO 4
<211> LENGTH: 18
<212> TYPE: DNA
<213> ORGANISM: Artificial
<220> FEATURE:
<223> OTHER INFORMATION: Synthetic -continued

<400> SEQUENCE: 4
ccaggccgaa cctgtcat 18

<210> SEQ ID NO 5
<211> LENGTH: 22
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Fam
<220> FEATURE:
<221> NAME/KEY: misc_feature
<222> LOCATION: (22)..(22)
<223> OTHER INFORMATION: Tamra

<400> SEQUENCE: 5
cgactgtgtg gtccggccca tc 22

<210> SEQ ID NO 6
<211> LENGTH: 20
<212> TYPE: DNA
<213> ORGANISM: Artificial
<220> FEATURE:
<223> OTHER INFORMATION: Synthetic

<400> SEQUENCE: 6
cattgcagtt ggcctggtaa 20

<210> SEQ ID NO 7
<211> LENGTH: 23
<212> TYPE: DNA
<213> ORGANISM: Artificial
<220> FEATURE:
<223> OTHER INFORMATION: Synthetic

<400> SEQUENCE: 7
ctttggcaag agagagctca agt 23

<210> SEQ ID NO 8
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Fam
<220> FEATURE:
<221> NAME/KEY: misc_feature
<222> LOCATION: (21)..(21)
<223> OTHER INFORMATION: Tamra

<400> SEQUENCE: 8
ccgatcaagg atgcgccatc a 21

<210> SEQ ID NO 9
<211> LENGTH: 20
<212> TYPE: DNA
<213> ORGANISM: Artificial
<220> FEATURE:
<223> OTHER INFORMATION: Synthetic

<400> SEQUENCE: 9

-continued gtcggagtcg tgacgctgta 20

<210> SEQ ID NO 10
<211> LENGTH: 21
<212> TYPE: DNA
<213> ORGANISM: Artificial
<220> FEATURE:
<223> OTHER INFORMATION: Synthetic

<400> SEQUENCE: 10
gttgatggcg catccttgat c 21

<210> SEQ ID NO 11
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Fam
<220> FEATURE:
<221> NAME/KEY: misc_feature
<222> LOCATION: (21)..(21)
<223> OTHER INFORMATION: Tamra

<400> SEQUENCE: 11
tgggagttat ggtgggcgcc g 21

<210> SEQ ID NO 12
<211> LENGTH: 25
<212> TYPE: DNA
<213> ORGANISM: Artificial
<220> FEATURE:
<223> OTHER INFORMATION: Synthetic

<400> SEQUENCE: 12
aaaacacttc catgtcattt tcatg 25

<210> SEQ ID NO 13
<211> LENGTH: 21
<212> TYPE: DNA
<213> ORGANISM: Artificial
<220> FEATURE:
<223> OTHER INFORMATION: Synthetic

<400> SEQUENCE: 13
gttgatggcg catccttgat c 21

<210> SEQ ID NO 14
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Fam
<220> FEATURE:
<221> NAME/KEY: misc_feature
<222> LOCATION: (33)..(33)
<223> OTHER INFORMATION: Tamra

<400> SEQUENCE: 14
tgcgatagga attatcacac tctatctggg agc 33

-continued

<210> SEQ ID NO 15
<211> LENGTH: 24
<212> TYPE: DNA
<213> ORGANISM: Artificial
<220> FEATURE:
<223> OTHER INFORMATION: Synthetic

<400> SEQUENCE: 15
cttagtattg tggattggca cgaa 24

<210> SEQ ID NO 16
<211> LENGTH: 21
<212> TYPE: DNA
<213> ORGANISM: Artificial
<220> FEATURE:
<223> OTHER INFORMATION: Synthetic

<400> SEQUENCE: 16
gcgccaactg tgaaacctag a 21

<210> SEQ ID NO 17
<211> LENGTH: 29
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Fam
<220> FEATURE:
<221> NAME/KEY: misc_feature
<222> LOCATION: (29)..(29)
<223> OTHER INFORMATION: Tamra

<400> SEQUENCE: 17
agaaacactt caatggcaat gacgtgcat 29

<210> SEQ ID NO 18
<211> LENGTH: 19
<212> TYPE: DNA
<213> ORGANISM: Artificial
<220> FEATURE:
<223> OTHER INFORMATION: Synthetic

<400> SEQUENCE: 18
tcgcaacagc cttaacagc 19

<210> SEQ ID NO 19
<211> LENGTH: 21
<212> TYPE: DNA
<213> ORGANISM: Artificial
<220> FEATURE:
<223> OTHER INFORMATION: Synthetic

<400> SEQUENCE: 19
actatctccc tcccatcctt c 21

<210> SEQ ID NO 20
<211> LENGTH: 16
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Fam
<220> FEATURE:

-continued

```
<221> NAME/KEY: misc_feature
<222> LOCATION: (16)..(16)
<223> OTHER INFORMATION: MGB/NFQ

<400> SEQUENCE: 20

ttcacaccac ttccac                                                    16


<210> SEQ ID NO 21
<211> LENGTH: 18
<212> TYPE: DNA
<213> ORGANISM: Artificial
<220> FEATURE:
<223> OTHER INFORMATION: Synthetic

<400> SEQUENCE: 21

aatgacagac acgactcc                                                  18


<210> SEQ ID NO 22
<211> LENGTH: 22
<212> TYPE: DNA
<213> ORGANISM: Artificial
<220> FEATURE:
<223> OTHER INFORMATION: Synthetic

<400> SEQUENCE: 22

cccaaaacct actatcttca ac                                             22


<210> SEQ ID NO 23
<211> LENGTH: 17
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Fam
<220> FEATURE:
<221> NAME/KEY: misc_feature
<222> LOCATION: (17)..(17)
<223> OTHER INFORMATION: MGB/NFQ

<400> SEQUENCE: 23

tggaagtcgg cacgtga                                                   17
```

METHOD OF IMMUNIZATION AGAINST THE 4 SEROTYPES OF DENGUE FEVER

CROSS-REFERENCE TO RELATED APPLICATIONS

This application claims priority to provisional application Ser. No. 60/885,077, which was filed on Jan. 16, 2007, and is hereby incorporated by reference in its entirety.

BACKGROUND OF THE INVENTION

1. Field of the Invention

The invention relates to a method for inducing protection against the 4 serotypes of dengue fever in a patient, comprising:

(a) a first administration of a monovalent vaccine comprising a vaccinal virus of a first serotype of dengue fever, (b) a second administration of a tetravalent vaccine comprising vaccinal viruses of the four serotypes of dengue fever, and in which the second administration (b) is made between at least 30 days and not more than 12 months after the first administration (a).

2. Summary of the Related Art

Dengue fevers are caused by four viruses of the flavivirus genus which are of similar serological type but differ from the antigen point of view (Gübler et al., 1988, in: Epidemiology of arthropod-borne viral disease. Monath T P M, editor, Boca Raton (Fla.): CRC Press: 223-60; Kautner et al., 1997, J. of Pediatrics, 131: 516-524; Rigau-Pérez et al., 1998, Lancet, 352: 971-977; Vaughn et al., 1997, J. Infect. Dis., 176: 322-30). Infection with a serotype of dengue fever may produce a spectrum of clinical disease from non-specific viral syndrome to severe fatal hemorrhagic disease. The incubation period for dengue fever after a mosquito bite is approximately 4 days (from 3 to 14 days). Dengue fever is characterized by a two-phase fever, headaches, pains in various parts of the body, prostration, eruptions and lymphadenopathy (Kautner et al., 1997, J. of Pediatrics, 131: 516-524; Rigau-Pérez et al., 1998, Lancet, 352: 971-977). The viremic period is of the same as the febrile period (Vaughn et al., 1997, J. Infect. Dis., 176: 322-30). Cure of dengue fever is complete after 7 to 10 days, but prolonged asthenia is normal. Reduced leukocyte and platelet numbers frequently occur.

Hemorrhagic dengue fever is a severe febrile disease characterized by homeostasis abnormalities and an increase in vascular permeability which can lead to hypovolemia and hypotension (dengue fever with shock syndrome), often complicated by severe internal bleeding. The mortality rate for hemorrhagic dengue fever can reach 10% without treatment, but is $\leqq$1% in most centers with experience of treatment (WHO Technical Guide, 1986. Dengue hemorrhagic fever: diagnosis, treatment and control, p. 1-2. World Health Organization, Geneva, Switzerland).

Routine laboratory diagnosis of dengue fever is based on isolation of the virus and/or the detection of antibodies specific to dengue fever virus.

Dengue is the second most important infectious tropical disease after malaria, more than half of the world's population living in areas where there is a risk of epidemic transmission. There are estimated to be 50-100 million cases of dengue fever every year, 500,000 patients hospitalized for hemorrhagic dengue fever, and 25,000 deaths. Dengue fever is endemic in Asia, the Pacific, Africa, Latin America and the Caribbean. Dengue fever virus infections are endemic in more than 100 tropical countries and hemorrhagic dengue fever has been documented in 60 of these countries (Gubler, 2002, TRENDS in Microbiology, 10: 100-103; Monath, 1994, Proc. Natl. Acad. Sci., 91: 2395-2400). A number of well-described factors would appear to be implicated in dengue fever—population growth, unplanned and uncontrolled urbanization, in particular associated with poverty, an increase in air travel, lack of effective mosquito control and deterioration of sanitary and public health infrastructure (Gubler, 2002, TRENDS in Microbiology, 10: 100-103). Travellers and expatriates are increasingly being warned about dengue fever (Shirtcliffe et al., 1998, J. Roy. Coll. Phys. Lond., 32: 235-237). Dengue fever has been one of the main causes of febrile diseases among American troops during deployments in tropical areas where dengue fever is endemic (DeFraites et al., 1994, MMWR, 1994, 43: 845-848).

The viruses are maintained within a cycle involving humans and *Aedes aegypti*, a domestic mosquito which bites during the daytime, and prefers to feed on man. Infection in man is initiated by injection of the virus during the blood meal of an infected *Aedes aegypti* mosquito. The salivary virus is mainly deposited in the extravascular tissues. The first category of cells to be infected after inoculation are the dentritic cells, which then migrate to the lymphatic ganglia (Wu et al., 2000, Nature Med., 7: 816-820). After initial replication in the skin and lymphatic ganglia, the virus appears in the blood in the course of the acute febrile stage, generally for 3 to 5 days.

Along with the dentritic cells, monocytes and macrophages are among the first targets of dengue fever virus. Protection against homotypic reinfection is complete and probably lasts a lifetime, but cross-protection between the different types of dengue lasts from less than a few weeks to a few months (Sabin, 1952, Am. J. Trop. Med. Hyg., 1: 30-50). As a consequence, an individual may become infected with a different serotype. A second infection due to dengue fever is in theory a risk factor for the development of severe dengue fever. However, hemorrhagic dengue fever is multifactorial—factors include the strain of virus involved and the age, immune status and genetic predisposition of the patient. Two factors play a major role in the occurrence of hemorrhagic dengue fever—rapid viral replication with a high level of viremia (the severity of the disease being associated with the level of viremia; Vaughn et al., 2000, J. Inf. Dis., 181: 2-9) and a major inflammatory response with the release of high levels of inflammatory mediators (Rothman and Ennis, 1999, Virology, 257: 1-6). There is no specific treatment against dengue fever. Treatment for dengue fever is symptomatic, with bed rest, control of the fever and pain through antipyretics and analgesics, and adequate drinking. The treatment of hemorrhagic dengue fever requires balancing of liquid losses, replacement of coagulation factors and the infusion of heparin.

Preventive measures are currently based on control of the vector and personal protection measures which are difficult to apply and are costly. No vaccine against dengue fever has at present been approved. Given that the four serotypes of dengue fever are in circulation in the world and that they have been reported as being involved in cases of hemorrhagic dengue fever, vaccination should ideally confer protection against the four serotypes of dengue fever virus.

When immunizing with a tetravalent vaccine, it may happen that the response is induced predominantly against only one or at most 3 serotypes. There is therefore a need for a method which makes it possible to reduce interference between the different serotypes and makes it possible to induce neutralizing antibodies against the 4 serotypes of dengue fever.

SUMMARY OF THE INVENTION

The inventors have found that it is possible to generate an immune response comprising antibodies neutralizing the 4 serotypes when the vaccinal formulation which is intended to induce a response against the 4 serotypes is administered after preliminary immunization with an attenuated living vaccine of only one serotype, the second immunization being made 30 days to 12 months after the first administration.

DETAILED DESCRIPTION OF THE PREFERRED EMBODIMENTS

The inventors have in particular shown that tetravalent DEN-1,2,3,4 immunization after monovalent DEN-2 immunization induces responses against the four serotypes in all the monkeys immunized. Conversely, tetravalent immunization alone only induced a satisfactory response against two out of 4 serotypes, even after a booster.

The immune response generated by the method according to the invention is therefore both quantitatively and qualitatively greater (covers all serotypes).

In accordance with a first object, this invention therefore relates to a method making it possible to induce a neutralizing antibody response against the 4 serotypes of dengue fever in a patient and comprises:

(a) a first administration of a monovalent vaccine comprising a vaccinal virus of a first serotype of dengue fever, (b) a second administration of a tetravalent vaccine comprising vaccinal viruses of the 4 serotypes of dengue fever, and in which the second administration (b) is made at least 30 days and not more than 12 months after the first administration (a).

According to a particular embodiment of the method of immunization according to the invention, the vaccinal virus used in the first administration (a) is selected from the group comprising vaccinal viruses of dengue fever of serotype 1 or 2.

According to another particular embodiment of the method of immunization according to the invention, the said vaccinal virus used in the first administration (a) is selected from the group comprising strains VDV1 and VDV2.

According to another particular embodiment of the method according to the invention, the said vaccinal viruses used in the tetravalent vaccine are Chimerivax™ DEN-1,2,3 and 4.

According to another particular embodiment of the method according to the invention the quantity of vaccinal viruses of dengue fever of serotypes 1, 2, 3 and 4 lies within a range from $10^3$ to $10^6$ $DICC_{50}$.

According to another particular embodiment of the method according to the invention, the monovalent vaccine comprises about $10^4$ $DICC_{50}$ of VDV1 or VDV2 and the tetravalent vaccine comprises about $10^5$ $DICC_{50}$ of Chimerivax™ DEN-1,2,3 and $10^3$ $DICC_{50}$ of Chimerivax™ DEN-4.

According to another embodiment of the method according to the invention, the second administration (b) is made 30 to 60 days after the first administration (a).

Another object of the present invention is an immunization kit against dengue fever virus comprising a container containing at least (a) a first container containing a monovalent composition or vaccine comprising a vaccinal virus of a first serotype of dengue fever, (b) a second container containing a tetravalent composition or vaccine comprising vaccinal viruses for the 4 serotypes of dengue fever.

According to one embodiment, the kit according to the invention comprises at least:

(a) a first container containing a monovalent vaccine comprising a VDV1 or VDV2 vaccinal virus, (b) a second container containing a tetravalent vaccine comprising the 4 Chimerivax™ DEN-1,2,3 and 4.

According to a particular embodiment, the kit according to the invention comprises a monovalent vaccine comprising about $10^4$ $DICC_{50}$ of VDV1 or VDV2 and a tetravalent vaccine comprising about $10^5$ $DICC_{50}$ of Chimerivax™ DEN-1, 2,3 and about $10^3$ $DICC_{50}$ of Chimerivax™ DEN-4.

This invention therefore also relates to use of dengue fever vaccinal viruses for the manufacture of a monovalent vaccine and a tetravalent vaccine for immunization against dengue fever virus in which the monovalent vaccine comprises a vaccinal virus of a first serotype of dengue fever, the tetravalent vaccine comprises vaccinal viruses of the 4 serotypes of dengue fever and in which the tetravalent vaccine is administered at least 30 days and not more than 12 months after administration of the monovalent vaccine.

The invention will now be described in more detail in the description which follows.

Definitions

"Dengue fever viruses" or "DEN" are positive single-strand RNA viruses belonging to the Flavivirus genus of the family of flaviviridae. The genome in RNA contains a type I end member at the 5' extremity but has no poly-A tail at the 3' extremity. The organization of the genome comprises the following elements: non-coding region (NCR) 5', structural proteins (capsid (C), pre-membrane/membrane (prM/M), envelope (E)) and non-structural proteins (NS1-NS2A-NS2B-NS3-NS4A-NS4B-NS5) and NCR 3'. The viral genome RNA is associated with the capsid proteins to form a nucleocapsid. As in the case of flaviviruses, the DEN viral genome codes an uninterrupted coding region which is translated into a single polyprotein.

In the context of this invention, by "vaccinal dengue fever virus" is meant any viral form of dengue fever virus that is capable of inducing a specific immune response comprising neutralizing antibodies, which preferably includes all viral forms of dengue fever virus which can be used in the context of an immunization program in man against infection by a dengue fever virus. By vaccinal dengue fever viruses are therefore meant inactivated viruses, attenuated viruses, and recombinant proteins such as the envelope protein of dengue fever virus. Numerous examples of these are known in the art.

A vaccinal virus is regarded as being "inactivated" if it no longer replicates in permissive cells.

A vaccinal virus is regarded as being "attenuated" if after growth at 37° C. or 39° C. in Huh-7, VERO and/or C6/36 liver cells the said vaccinal virus has a maximum titer which is at least 10 times less than maximum titer obtained with the wild parent strain under the same culture conditions and as measured using the same method for determining titer. A vaccinal virus which has diminished growth in at least one of the three cell types identified above is therefore regarded as being "attenuated" in the context of this invention.

A vaccinal virus which can be used in man has a positive benefit/risk ratio, the said ratio generally satisfying statutory and regulatory requirements for obtaining a marketing authorization. A vaccinal dengue fever virus used in the context of this invention is preferably a virus which has been attenuated in such a way that it does not induce the disease in man. Advantageously, the said vaccinal virus only results in side effects of at most moderate intensity (i.e., medium to slight, or zero) in the majority of vaccinated individuals, while retaining its ability to induce a neutralizing antibody response.

Dengue fever vaccinal viruses which can be used in the context of this invention may be cited by way of non-limiting examples: inactivated vaccinal viruses, attenuated vaccinal viruses such as the attenuated strains VDV-1, VDV-2, the strains described for example in applications WO02/66621, WO0057904, WO0057908, WO0057909, WO0057910, WO02/0950075 and WO02/102828, or chimeras. Chimeric viruses have the special feature that they have the characteristics of attenuated viruses as defined above. All chimeric viruses expressing the envelope protein of a dengue fever virus and inducing an immune response comprising antibodies neutralizing the serotype from which the envelope protein originates may therefore be used in the context of this invention. Mention may be made by way of non-limiting examples of: the dengue fever Chimerivax™ such as described for example in patent application WO 98/37911, dengue/dengue fever chimeras such as described for example in patent applications WO9640933 and WO0160847. The vaccinal virus of serotype 1 dengue fever may for example be the vaccinal strain VDV1 or a Chimerivax™ DEN-1, in particular a YF17D/DEN-1 virus, or again a DEN-1 16007/PDK13 strain. The vaccinal virus for serotype 2 of dengue fever may for example be the vaccinal strain VDV2 or a Chimerivax™ DEN-2, in particular a YF17D/DEN-2 virus, or again a DEN-2 16681/PDK53 strain. The vaccinal virus of serotype 3 of dengue fever may be a Chimerivax™ DEN-3, in particular a YF17D/DEN-3 virus. The vaccinal virus of serotype 4 of dengue fever may be a Chimerivax™ DEN-4, in particular a YF17D/DEN-4 virus. Reference may be made to the applications identified here for precise description of the strains mentioned and the processes for obtaining them.

"VDV" or "Vero dengue vaccine" designates an attenuated living dengue fever viral strain adapted to Vero cells (i.e. able to reproducibly replicate at significant level in Vero cells) and capable of inducing a specific humoral response, including the induction of neutralizing antibodies, in primates and particularly in man.

"VDV-1" is a strain obtained from a wild DEN-1 16007 strain which has undergone 11 passes through PDK cells (DEN-1 16007/PDK11) and which has subsequently been amplified in Vero cells at 32° C., the RNA of which has been purified and transfected in Vero cells. The VDV-1 strain has 14 additional mutations in comparison with the DEN-1 16007/PDK13 vaccinal strain (13 passes through PDK—Primary Dog Kidney-cells). The DEN-1 16007/PDK13 strain, also called "LAV1", has been described in patent application EP1159968 in the name of Mahidol University and has been filed with the National Microorganisms Cultures Collection (CNCM) under number I-2480. The complete sequence of the VDV-1 strain is given in sequence SEQ ID NO:1. This strain can easily be reproduced from that sequence. A process for preparing and characterizing the VDV-1 strain has been described in the international patent application filed under number WO/2006/134433 in the names of Sanofi-Pasteur and the Center for Disease Control and Prevention.

"VDV-2" is a strain which has been obtained from wild strain DEN-2 16681 which has undergone 50 passes through PDK cells (DEN-2 16681/PDK50), plate purified, the RNA from which has been extracted and purified before being transfected in Vero cells. The VDV-2 strain has subsequently been obtained by plate purification and amplification in Vero cells. The VDV-2 strain has 10 additional mutations in comparison with the DEN-2 16681/PDK53 vaccinal strain (53 passes through PDK cells), including 4 silent mutations. The DEN-2 16681/PDK53 strain, also known as "LAV2", has been described in patent application EP1159968 in the name of Mahidol University and has been filed with the National Microorganisms Cultures Collection (CNCM) under number I-2481. The complete sequence of the VDV-2 strain is given in sequence SEQ ID NO:2. The VDV-2 strain can easily be reproduced from that sequence. A process for preparing and characterizing the VDV-2 strain has been described in the international patent application filed under number WO/2006/134443 in the names of Sanofi-Pasteur and the Center for Disease Control and Prevention.

The VDV 1 and 2 strains are prepared by amplification in Vero cells. The viruses produced are harvested and clarified from cell debris by filtration. The DNA is digested by treatment with enzymes. Impurities are eliminated by ultrafiltration. Infectious titers may be increased by a concentration method. After adding a stabilizer, the strains are stored in lyophilized or frozen form before use and then reconstituted when needed.

By "ChimeriVax™ dengue" or "CYD" is meant a chimeric yellow fever (YF) virus which comprises the skeleton of a YF virus in which the sequences coding for the pre-membrane and envelope proteins have been replaced by those of a DEN virus. Thus, a chimeric YF virus containing the prM and E sequences of a serotype 1 dengue fever strain (DEN-1) is called "CYD-1 or CYD DEN1". A chimeric YF containing the prM and E sequences of a DEN-2 strain is referred to as "CYD-2 or CYD DEN2". A chimeric YF virus containing the prM and E sequences of a DEN-3 strain is referred to as "CYD-3 or CYD DEN3". A chimeric YF virus containing the prM and E sequences of a DEN-4 strain is referred to as "CYD-4 or CYD DEN4". The preparation of these dengue ChimeriVax™ has been described in detail in international patent applications WO 98/37911 and WO 03/101397, to which reference may be made for a precise description of the processes for their preparation. The chimeras described in the examples have been generated by using prM and E sequences from strains DEN 1 PUO359 (TYP1140), DEN2 PUO218, DEN3 PaH881/88 and DEN 4 1228 (TVP 980). Any dengue fever virus strain may be used to construct chimeras in the context of this invention.

Preferably, the chimeric YF virus comprises the skeleton of an attenuated yellow fever strain YF17D (Theiler M. and Smith H. H. (1937) J. Exp. Med., 65, p. 767-786) (viruses YF17D/DEN-1, YF17D/DEN-2, YF17D/DEN-3, YF17D/DEN-4). Examples of YF17D strains which may be used include YF17D204 (YF-Vax®, Sanofi-Pasteur, Swifwater, Pa., USA; Stamaril®, Sanofi-Pasteur, Marcy l'Etoile, France; ARILVAX™, Chiron, Speke, Liverpool, UK; FLA-VIMUN™, Berna Biotech, Bern, Switzerland; YF17D-204 France (X15067, X15062); YF17D-204,234 US (Rice et al., 1985, Science, 229: 726-733), or again the related strains YF17DD (Genbank access number U17066), YF17D-213 (Genbank access number U17067) and the strains YF17DD described by Galler et al. (1998, Vaccines, 16(9/10): 1024-1028). Any other attenuated yellow fever virus strain which may be used in man may be used to construct chimeras in the context of this invention.

When the term "about" is used in conjunction with an amount it means plus or minus 10% of that amount, e.g., "about $10^4$" means $10^4 \pm 10^3$.

According to a particular embodiment, for each serotype used in the various administrations the vaccinal viruses are present in the vaccine in a quantity from $10^3$ to $10^5$ $DICC_{50}$.

According to a particular embodiment, vaccinal viruses VDV1 or VDV2 are present in the monovalent vaccine at a level of about $10^4$ $DICC_{50}$.

According to a particular embodiment, Chimerivax™ DEN-1, 2, 3 are present in the tetravalent vaccine at a level of about $10^5$ $DICC_{50}$ and Chimerivax™ DEN-4 is present in the tetravalent vaccine at a level of about $10^3$ $DICC_{50}$.

Each monovalent ChimeriVax™ dengue fever vaccinal virus (serotypes 1, 2, 3 and 4) has been prepared by amplifying each serotype in Vero cells. More specifically, the four viruses are produced separately in adhering Vero cells in a serum-free medium. The viral harvest, clarified from cell debris by filtration, is then concentrated and purified by ultrafiltration and chromatography to remove the DNA from the host cells. After adding a stabilizing agent, the vaccinal strains are stored in a frozen or lyophilized form before use and then reconstituted as needed. The same process is applied to the four chimeras.

A dose, composition or vaccine is "monovalent" when in addition to a pharmaceutically acceptable excipient it contains a vaccinal virus of a single dengue fever serotype. A dose, composition or vaccine is "tetravalent" when it contains vaccinal viruses of the four serotypes of dengue fever. Multivalent compositions are obtained by simple mixing of monovalent compositions.

By "patient" is meant a person (child or adult) who is likely to be infected by dengue fever, in particular a person at risk of infection, such as for example a person traveling in regions where dengue fever is present, or an inhabitant of those regions. The term therefore includes persons who are naïve for dengue fever virus and those who are not naïve.

Tetravalent Immunization Following Initial Monovalent Immunization

In a first aspect, this invention therefore relates to a method of immunization against dengue fever virus.

The inventors have in fact shown in particular that the administration of 4 serotypes 30 days to 12 months after the first administration of a monovalent vaccine makes it possible to obtain effective protection against the 4 serotypes. The method according to this invention is therefore of very particular interest in the context of an immunization strategy against dengue fever.

According to this invention, the first immunization may be performed using a monovalent composition or vaccine comprising a vaccinal virus of any of the 4 serotypes of dengue fever, the second administration being performed with all 4 vaccinal serotypes. According to a particular embodiment, a serotype 1 or 2 dengue fever vaccinal virus, preferably serotype 2, is used for the first administration. Preferably, the dengue fever vaccinal virus used in the first administration is an attenuated dengue virus and is not a chimeric virus. According to a particular embodiment, strain VDV1 or VDV2, preferably strain VDV2, is used as the vaccinal virus in the first administration.

Attenuated living vaccinal viruses are used in the second administration, preferably chimeric viruses expressing antigens for the four serotypes of dengue fever virus, in particular Chimerivax™ DEN1, 2, 3 and 4.

According to particular embodiments, this invention therefore includes the following systems:

(a) VDV1 (b) CYD DEN-1, 2, 3 and 4

(b) VDV2 (b) CYD DEN-1, 2, 3 and 4.

In the context of this invention, by "vaccinal composition" is meant a composition comprising an "immunoeffective quantity" of dengue fever vaccinal virus, that is to say a sufficient quantity of dengue fever vaccinal virus to induce a specific immune response comprising neutralizing antibodies, which may be revealed for example by the seroneutralization test as described in Example 1 below. A serum is regarded as being positive for the presence of neutralizing antibodies when the titer of neutralizing antibodies so determined is not less than 1:10 (unity: 1/dilution).

The quantities of vaccinal strain are commonly expressed in terms of viral plaque forming units (PFU) or doses infecting 50% of the tissue culture or again doses infecting 50% of the cell culture ($DICC_{50}$). For example, compositions according to the invention may contain 10 to $10^6$ $DICC_{50}$, in particular $10^3$ to $10^5$ $DICC_{50}$ of dengue fever vaccinal virus of serotypes 1, 2, 3 or 4 for a monovalent or tetravalent composition. Thus, in the compositions or utilizations according to the invention the doses of dengue vaccinal viruses of serotypes 1, 2, 3 and 4 preferably each lie within a range from 10 to $10^6$ $DICC_{50}$, such as 10, $10^2$, $10^3$, $10^4$, $10^5$ or $10^6$ $DICC_{50}$, in particular within a range from $10^3$ to $10^5$ $DICC_{50}$. Vaccinal virus may be used at the same or different doses, which can be adjusted in relation to the nature of the vaccinal virus used and the intensity of the immune response obtained.

According to a particular embodiment of a method according to this invention, the quantities of attenuated live vaccinal virus in monovalent and tetravalent compositions or vaccines are $10^3$ to $10^5$ $DICC_{50}$. According to a particular embodiment, the monovalent vaccine comprises about $10^4$ $DICC_{50}$ of VDV1 or VDV2, preferably VDV2. According to a particular embodiment, the tetravalent vaccine comprises $10^5$ $DICC_{50}$ of Chimerivax™ DEN-1, 2, 3 and 4. According to one advantageous embodiment, the tetravalent vaccine comprises about $10^5$ $DICC_{50}$ of Chimerivax™ DEN-1, 2 and 3 and about $10^3$ $DICC_{50}$ of Chimerivax™ DEN-4.

In the context of this invention, the second administration (b) is performed 30 days and not more than 12 months after administration (a). According to an advantageous embodiment, the second administration is performed 30 days to 60 days after the first administration (a).

The neutralizing antibody response is advantageously durable, that is to say it can be detected in serum up to at least 6 months after the second administration.

Vaccinal viruses are administered in the form of compositions or vaccines which can be prepared by any method known to those skilled in the art. Normally, viruses, generally in lyophilized form, are mixed with a pharmaceutically acceptable excipient such as water or a phosphate-buffered saline solution, wetting agents or stabilizing agents. By "pharmaceutically acceptable excipient" is meant any solvent, dispersing medium, charge, etc., which does not produce any secondary reaction, for example an allergic reaction, in humans or animals. The excipient is selected on the basis of the pharmaceutical form chosen, the method and the route of administration. Appropriate excipients, and requirements in relation to pharmaceutical formulation, are described in "Remington: The Science & Practice of Pharmacy", which represents a reference work in the field.

Preferably, vaccinal compositions are prepared in injectable form, and may take the form of liquid solutions, suspensions or emulsions. The compositions may in particular comprise an aqueous solution buffered in such a way as to maintain a pH between about 6 and 9 (as determined using a pH meter at ambient temperature).

Although it is not necessary to add an adjuvant, the compositions may nevertheless include such a compound, that is to say a substance which increases, stimulates or reinforces the cell or humoral immune response induced by the vaccinal virus administered simultaneously. Those skilled in the art will be able to select an adjuvant which might be appropriate in the context of this invention from the adjuvants conventionally used in the field of vaccines.

The compositions or vaccines according to the invention may be administered by any means conventionally used in vaccination, for example parenterally (in particular intradermally, subcutaneously or intramuscularly), advantageously subcutaneously. Preferably, the compositions or vaccines are injectable compositions administered subcutaneously, advantageously in the region of the left deltoid or right deltoid.

The volume of vaccine composition administered will depend on the method of administration. In the case of subcutaneous injections, the volume is generally between 0.1 and 1.0 ml, preferably about 0.5 ml.

The optimum period for administering all serotypes 1 to 4 is about 1 to 3 months before exposure to dengue fever virus. Vaccinations may be administered as a prophylactic treatment against infection by dengue fever virus in adults and children. Target populations therefore include persons who may be naïve (i.e., not previously immunized) or non-naïve with regard to dengue fever virus.

Booster administrations of dengue fever vaccinal viruses of serotypes 1 to 4 may also be used for example between 6 months and 10 years, for example 6 months, 1 year, 3 years, 5 years or 10 years after administration of the second administration (b) according to the invention. Booster administrations will advantageously be performed using the same compositions or vaccines (i.e., the same vaccinal viruses) and preferably under the same conditions of administration (anatomical sites and methods of administration) as used for the 2$^{nd}$ administration (b).

Interference phenomena may be explained by the dominance of one or more serotypes in relation to others and are therefore independent of the technology used for preparation of the candidate vaccine (from VDV or Chimerivax™). The method according to this invention can therefore be applied in general to all dengue fever vaccinal viruses.

This invention is therefore also intended to cover use of dengue fever vaccinal viruses for the manufacture of a monovalent vaccine and a tetravalent vaccine for immunization against dengue fever virus in which the monovalent vaccine comprises the vaccinal virus of a first serotype of dengue fever, the tetravalent vaccine comprises vaccinal viruses for 4 serotypes of dengue fever, in which the tetravalent vaccine is administered at least 30 days and not later than 12 months after administration of the monovalent vaccine.

For a description of the vaccines and conditions of use in the context of use according to this invention, reference may be made to the description provided in relation to the method of immunization according to the invention.

According to another aspect, this invention has as its object an immunization kit against the four serotypes of dengue fever virus. The kit according to this invention comprises compositions or vaccines as defined above in relation to the method of immunization proposed. The kit according to the invention therefore comprises a container containing various containers containing the compositions or vaccines and advantageously, and optionally, an explanatory brochure including useful information for administration of the said compositions or vaccines.

According to one embodiment, this invention therefore relates to a kit for immunization against dengue fever virus, a container containing at least (a) a first container containing a monovalent vaccine comprising a vaccinal virus of a first serotype of dengue fever, and (b) a second container containing a tetravalent vaccine comprising vaccinal viruses for the 4 serotypes of dengue fever.

For a description of the vaccines, compositions or dengue fever vaccinal viruses which may be used in the kit according to the invention, reference may be made to the description provided above in relation to the method of immunization according to the invention.

According to a particular embodiment the kit according to the invention comprises at least:

(a) a first container containing a monovalent vaccine comprising a VDV1 or VDV2 vaccinal virus, and (b) a second container containing a tetravalent vaccine comprising the 4 Chimerivax™ DEN-1, 2, 3 and 4.

According to a particular embodiment, the kit according to the invention comprises at least one monovalent vaccine comprising about $10^4$ $DICC_{50}$ of VDV1 or VDV2 and a tetravalent vaccine comprising about $10^5$ $DICC_{50}$ of Chimerivax™ DEN-1, 2, 3 and about $10^3$ $DICC_{50}$ of Chimerivax™ DEN-4.

The kits according to the invention may contain a single example or several examples of the containers as described above.

If the vaccines used are in lyophilized form, the kit will advantageously comprise at least one additional container containing the diluent which can be used to reconstitute an injectable dose of vaccine. Any pharmaceutically acceptable diluent may be used for this purpose, conventionally water or a phosphate-buffered aqueous solution.

The invention is illustrated by the following example.

EXAMPLE 1

Immunization Against the 4 Serotypes of Dengue Fever Virus by Successive Injection of a Monovalent Composition Followed by a Tetravalent Composition in Monkeys Viremia and immunogenicity were tested in a monkey model. Viremia in particular has been identified as being one of the factors associated with the virulence and severity of the disease in man, and therefore constitutes an important parameter which must be taken into consideration. As for immunogenicity, this is a key parameter in the context of evaluating the protection imparted.

1.1 Materials and Methods

Experiments on monkeys were carried out in accordance with European Directives relating to animal experiments. The immunizations were performed on cynomolgus monkeys (*Macaca fascicularis*) originating from Mauritania. The monkeys were placed in quarantine for six weeks prior to immunization.

The monkeys were immunized subcutaneously with 0.5 ml of vaccine composition in the arm. After mild anesthesia with ketamine (Imalgene, Merial), blood was collected by puncture of the inguinal or saphenal veins. On days 0 and 28 following each immunization, 5 ml of blood were sampled in order to evaluate antibody responses, while between days 2 and 10 1 ml of blood was sampled in order to evaluate viremia. The blood was collected on ice and preserved on ice until the serum was separated off. In order to do this, the blood was centrifuged for 20 minutes at 4° C. and the serum collected was stored at −80° C. until the time of the tests.

Measurement of Viremia

Post-vaccination viremia was monitored by quantitative real time RT-PCT (qRT-PCR). Two sets of primers and probes located in the NS5 gene of the DEN1 and DEN2 strains were used to quantify the RNA of VDV-1 and VDV-2 respectively. A third set of 2 primers and 1 probe located in the NS5 gene of the YF virus was used to quantify the RNA of CYD. Finally, 4 sets of primers and specific probes for the different CYD serotypes located at the junction of the E (DEN)/NS1 (YF) genes were used to identify the serotype in the samples positive for NS5 YF RNA (see also Table 1). 7 plasmids containing the region targeted by each PCR, under the control of promoter T7, were transcribed in vitro to generate a series of synthetic RNA which were included in each RT-PCT test as an internal reference. The synthetic RNA were determined by spectrophotometry, the quantity of RNA obtained was converted into the number of RNA copies and expressed as GEQ (genome equivalents).

0.140 ml of monkey serum were extracted using the "Nucleospin 96 virus™" RNA extraction kit from Macherey Nagel according to the manufacturer's instructions, and then the purified RNA was eluted with 0.140 ml (0.090 ml, then 0.05 ml) of RNase-free water. In order to avoid repeated freeze/thaw cycles, a first quantification was performed immediately after extraction on 5 μl of the said RNA preparation. The remaining volume was frozen at 70° C.

In addition to the components of the "Qiagen Qauntitect™ probes" RT-PCR quantification kit (Qiagen), the reaction mixtures contained 10 picomoles of each primer, 4 picomoles of each probe and 5 μl of RNA in a total volume of 25 μl. In the case of the RNA under test, 5 μl of the purified preparation were added directly to the reaction mixture without a prior dilution stage. The synthetic RNAs were diluted 1/10 in RNAse-free water, and 7 dilutions containing approximately 10 to $10^6$ GEQ in 5 μl were quantified in parallel in order to generate a calibration curve.

The quantification reactions were carried out using the ABIPrism 700™ equipment from Applied Biosystem, using the following program: 50° C./30 min, 95° C./15 min, followed by 40 cycles of 95° C./15 sec −60° C./60 sec.

The quantification limit for viral RNA in this test is 2.9 to 3.3 $\log_{10}$GEQ/ml (800 to 2000 GEQ/ml; 4 to 10 GEQ/reaction), according to PCR targets (standard deviation: ±0.3 $\log_{10}$).

The correlation between infectious titer and the quantification of viral RNA was established in parallel with the tests by analyzing 0.140 ml of samples of negative monkey serums (DO) to which a known quantity of infectious particles of the viruses used for immunization (CYD or VDV) had been added. The said control serums were prepared in two dilutions containing approximately 1 PFU and approximately 100 PFU in 5 μl (2.3 and 4.3 $\log_{10}$PFU/ml, respectively).

In the tests used in the examples, the correlation between GEQ and PFU is as follows: GEQ/PFU ratio 2.7 $\log_{10}$ (i.e. 1 PFU=500 GEQ) for sera positive for YF or CYDs; GEQ/PFU ratio 2.5 $\log_{10}$ (i.e. 1 PFU=320 GEQ) for sera positive for VDV1 or VDV2.

The quantification limits are <3.3 $\log_{10}$GEQ/ml (i.e. <4 PFU/ml) for YF and CYDs qRT-PCR, and <2.9 $\log_{10}$GEQ/ml (i.e. <2.5 PFU/ml) for VDV1 and VDV2 qRT-PCR.

The primers and probes used are shown in Table 1 below, in which the sense and anti-sense primers and the probe are listed in order for each test.

Measurement of Neutralizing Antibodies (Seroneutralization Test) (SN50)

Conventionally, dengue fever antibodies are measured using the PRNT50 test (test of neutralization by reducing the number of PFU to 50%). As this test is cumbersome and consumes much material, we have developed the SN50 test based on a 50% reduction in the number of units measured in the DICC50 test.

In a 96 well plate, 0.120 ml of each decomplemented serum is added to 0.480 ml of diluent (ISCOVE 4% SVF) in each well. Serial dilutions of a factor 6 are performed by transferring 0.150 ml of serum into 0.450 ml of diluent. 450 μl of viral dilution containing 2.7 $\log_{10}$ DICC50/ml are added to each well so as to obtain 25 DICC50/well. The plate is incubated at 37° C. for 1 hour. 0.1 ml of each dilution is then distributed into 6 wells of a 96 well plate in which VERO cells have been seeded 3 days before the start of the experiment at a density of 8000 cells/well in 0.1 ml of ISCOVE 4% SVF medium. After 6 days incubation at 37° C. in the presence of 5% $CO_2$, the cells are fixed using an ethanol/acetone (70/30) mixture at 4° C. for 15 minutes, and then washed 3 times in PBS and incubated for 1 hour at 37° C. in the presence of 0.05 ml of a 1/2000 dilution of an anti-flavivirus monoclonal antibody (mAb 4G2 obtained from an ATCC H-B112 hybridoma). The plates are then washed twice and incubated for 1 hour at 37° C. in the presence of 0.05 ml of a 1/1000 dilution of an anti-mouse IgG conjugated with alkaline phosphatase. The lysis plaques are revealed by adding 0.05 ml of a stained substrate: BCIP/NBT. The neutralizing antibody titers are calculated using the Karber formula as defined below:

$$\mathrm{Log}_{10}SN50=d+f/N(X+N/2),$$

in which:

d: represents the dilution providing 100% neutralization (that is 6 negative replicates, i.e. presenting no signs of infection)

f: represents the dilution factor as $\log_{10}$ (e.g. dilution factor of 1:4, f=0.6)

N: represents the number of replicates/dilution (N=6)

TABLE 1

| | | | | |
|---|---|---|---|---|
| Y | YF-NS5 | sense | 5' GCACGGATGTAACAGACTGAAGA (23 bases) | SEQ ID NO: 3 |
| F | YF NS5 | antisense | 5' CCAGGCCGAACCTGTCAT (18 bses) | SEQ ID NO: 4 |
| | YF-NS5 | | 5' Fam-CGACTGTGTGGTCCGGCCCATC-Tamra (22 bases) | SEQ ID NO: 5 |
| CYD1 | CYD1- | sense | 5' CAT TGC AGT TGG CCT GGT AA (20 b) | SEQ ID NO: 6 |
| spe | CYD1- | antisense | 5' CTT TGG CAA GAG AGA GCT CAA GT (23 b) | SEQ ID NO: 7 |
| | CYD1- | | 5' Fam-CCG ATC AAG GAT GCG CCA TCA-Tamra (21 b) | SEQ ID NO: 8 |
| CYD2 | CYD2- | sense | 5' GTG GGA GTC GTG ACG CTG TA (20 b) | SEQ ID NO: 9 |
| spe | CYD2- | antisense | 5' GTT GAT GGC GCA TCC TTG ATC (21 b) | SEQ ID NO: 10 |
| | CYD2- | | 5' Fam-TGG GAG TTA TGG TGG GCG CCG-Tamra (21 b) | SEQ ID NO: 11 |
| CYD3 | CYD3- | sense | 5' AAA ACA CTT CCA TGT CAT TTT CAT G (25 b) | SEQ ID NO: 12 |
| spe | CYD3- | antisense | 5' GTT GAT GGC GCA TCC TTG ATC (21 b) | SEQ ID NO: 13 |
| | CYD3- | | 5' Fam-TGCGATAGGAATTATCACACTCTATCTGGGAGC-Tamra (33 b) | SEQ ID NO: 14 |
| CYD4 | CYD4- | sense | 5' CTT AGT ATT GTG GAT TGG CAC GAA (24 b) | SEQ ID NO: 15 |
| spe | CYD4- | antisense | 5' GCG CCA ACT GTG AAA CCT AGA (21 b) | SEQ ID NO: 16 |
| | CYD4- | | 5'-Fam-AGAAACACTTCAATGGCAATGACGTGCAT-Tamra (29 b) | SEQ ID NO: 17 |
| VDV1 | VDV1-NS5 | sense | 5' TCG CAA CAG CCT TAA CAG C (19 b) | SEQ ID NO: 18 |
| spe | VDV1-NS5 | antisense | 5' ACT ATC TCC CTC CCA TCC TTC (21 b) | SEQ ID NO: 19 |
| | VDV1-NS5 | | 5' Fam-TTC ACA CCA CTT CCA C-M GB/NFQ (16 b) | SEQ ID NO: 20 |
| VDV2 | VDV2-NS5 | sense | 5' AAT GAC AGA CAC GAC TCC (18 b) | SEQ ID NO: 21 |
| spec | VDV2-NS5 | antisense | 5' CCC AAA ACC TAC TAT CTT CAA C (22 b) | SEQ ID NO: 22 |
| | VDV2-NS5 | | 5' Fam-TGG AAG TCG GCA CGT GA-MGB/NFQ (17 b) | SEQ ID NO: 23 |

X: total number of wells having no sign of infection, with the exception of dilution d.

The limit for viral detection is 10 SN50 (i.e. 1.0 $\log_{10}$SN50).

The viral strains used for neutralization were the strains DEN1 16007, DEN2 16681, DEN3 16562 or DEN4 1036.

In the case of the controls, the initial viral dilutions were re-titrated.

The correlation between the neutralizing titer measured in the SN50 test and the neutralizing titer measured conventionally in the PRNT50 test is: $\log_{10}$PRNT50=$\log_{10}$SN50+0.2.

1.2 Evaluation of Simultaneous Immunizations 2 groups of 4 monkeys of equivalent age and weight were immunized (see Table 2).

Immunization was performed subcutaneously in the arm using a 23G1 needle, with a quantity of $10^5$ $DICC_{50}$ for each CYD DEN 1 to 4 serotype for the tetravalent vaccine and a quantity of $10^4$ $DICC_{50}$ for the monovalent VDV-2.

TABLE 2

| Composition of the groups and immunization protocol Monkeys | | |
|---|---|---|
| | Immunizations | |
| Group | D0 | D56 |
| Group 1 | Monovalent VDV 2 | Tetravalent Dengue 1234 ChimeriVax |
| Group 2 | Tetravalent Dengue 1234 ChimeriVax | Tetravalent Dengue 1234 ChimeriVax |

The immunogenicity results obtained after one immunization (D0+28) and two immunizations (D56+28) are shown in Table 3.

The viremia results are provided in Table 4.

TABLE 3

| Monkeys | | | SN50 neutralizing titer (units 1/dil) | | | | | | | |
|---|---|---|---|---|---|---|---|---|---|---|
| | Immunizations | | D0 + 28 | | | | D56 + 28 | | | |
| ID | D0 | D56 | DEN-1 | DEN-2 | DEN-3 | DEN-4 | DEN-1 | DEN-2 | DEN-3 | DEN-4 |
| AM762 | VDV 2 | CYD | 10 | 501 | — | 10 | 63 | 1005 | 63 | 200 |
| AM839 | | 1234 | — | 802 | — | — | 80 | 1271 | 63 | 504 |
| AM905 | | | 20 | 158 | — | — | 318 | 1010 | 252 | 506 |
| AN011 | | | 13 | 1005 | — | — | 252 | 1271 | 319 | 1010 |
| Geometric mean | | | 11 | 503 | <10 | <10 | 142 | 1131 | 134 | 477 |
| AM496 | CYD | CYD | 50 | — | 16 | 32 | 100 | 40 | 80 | 252 |
| AM645 | 1234 | 1234 | — | — | 13 | 31 | 16 | — | — | 63 |
| AM766 | | | — | — | — | 32 | 20 | — | — | 80 |
| AM813 | | | 25 | — | — | 13 | 63 | 13 | 20 | 63 |
| Geometric mean | | | 13 | <10 | <10 | 25 | 38 | 11 | 14 | 95 |

—: titer < 10

TABLE 4

| viremia analyses (units: log10 GEQ/mL) | | | | | | | | | | |
|---|---|---|---|---|---|---|---|---|---|---|
| | | First immunization | | | | | | | | |
| Group | Monkey | D2 | D3 | D4 | D5 | D6 | D7 | D8 | D9 | D10 |
| 1 | AM762 | <2.7 | <2.7 | <2.7 | <2.7 | **4.77** | **4.89** | **4.84** | **4.47** | <2.7 |
| initial VDV 2 | AM839 | **5.11** | **4.51** | **4.19** | **4.19** | **4.56** | **3.69** | <2.7 | <2.7 | <2.7 |
| booster CYD 1, 2, 3, 4 | AM905 | <2.7 | <2.7 | <2.7 | <2.7 | **4.16** | **4.31** | **4.16** | **3.50** | **4.14** |
| | AN011 | <2.7 | <2.7 | **3.75** | **4.29** | **4.35** | **4.22** | **3.51** | <2.7 | **3.28** |
| 2 | AM496 | 4.22 | 3.36 | 3.71 | 4.15 | 3.14 | <3.1 | 3.58 | <3.1 | <3.1 |
| initial CYD 1, 2, 3, 4 | AM645 | **4.21** | 3.61 | 2.82 | 3.51 | 3.65 | 3.24 | <3.1 | 3.47 | 3.44 |
| booster CYD 1, 2, 3, 4 | AM766 | 3.97 | 3.06 | 3.38 | 4.19 | 3.80 | 3.73 | <3.1 | <3.1 | <3.1 |
| | AM813 | 4.81 | 4.60 | 3.17 | <3.1 | <3.1 | <3.1 | <3.1 | <3.1 | <3.1 |
| | | Booster | | | | | | | | |
| Group | Monkey | D58 | D59 | D60 | D61 | D62 | D63 | D64 | D65 | D66 |
| 1 | AM762 | <3.2 | <3.2 | <3.2 | 3.11 | <3.2 | <3.2 | 3.65 | 3.59 | <3.2 |
| initial VDV 2 | AM839 | 4.98 | 4.86 | 4.43 | 3.79 | <3.2 | <3.2 | <3.2 | <3.2 | <3.2 |
| booster CYD 1, 2, 3, 4 | AM905 | <3.2 | <3.2 | 3.09 | 3.42 | 3.39 | <3.2 | <3.2 | 4.08 | 4.22 |
| | AN011 | 3.55 | 3.42 | <3.2 | <3.2 | 3.42 | 3.37 | 4.67 | 5.09 | 4.97 |
| 2 | AM496 | <3.2 | <3.2 | <3.2 | <3.2 | <3.2 | <3.2 | <3.2 | <3.2 | <3.2 |
| initial CYD 1, 2, 3, 4 | AM645 | <3.2 | <3.2 | <3.2 | <3.2 | <3.2 | <3.2 | <3.2 | <3.2 | <3.2 |

TABLE 4-continued

| viremia analyses (units: log10 GEQ/mL) | | | | | | | | | | |
|---|---|---|---|---|---|---|---|---|---|---|
| booster CYD 1, 2, 3, 4 | AM766 | <3.2 | <3.2 | <3.2 | <3.2 | <3.2 | <3.2 | <3.2 | <3.2 | <3.2 |
| | AM813 | <3.2 | <3.2 | <3.2 | <3.2 | <3.2 | <3.2 | <3.2 | <3.2 | <3.2 |

CYD1
CYD4
VDV2

In brief, the results can be summarized as follows:

- The method of administration according to this invention brings about a qualitative and quantitative increase in the neutralizing antibody response obtained with a system comprising two identical immunizations with tetravalent vaccine.
- One CYD-1,2,3,4 immunization performed after an initial monovalent VDV2 immunization induces high level responses against the four serotypes in all the monkeys, unlike a system comprising 2 immunizations of tetravalent vaccine.
- As expected, the initial immunization performed with VDV2 induces a response which is almost exclusively directed against serotype 2, with a low level of cross-reactivity against serotypes 1 and 4 in some animals.
- Viremia is observed with VDV2 after initial immunization, and is predominantly caused by CYD-4 after the second administration (b) (group 1). No noteworthy differences were observed in the viremia induced after a first immunization with tetravalent vaccine in naïve animals (group 2). It can therefore be concluded that the system proposed by the invention does not encourage the emergence of viremia of serotypes 1, 3 and 4 after the second administration.

The examples therefore show that the method of immunization according to this invention improves the immunogenicity of the dengue fever vaccinal viruses without adversely affecting the latter's safety.

All publications recited herein are hereby incorporated by reference in their entirety. To the extent of conflict between a publication and the present specification, the present specification controls.

The invention claimed is:

1. A method of inducing neutralizing antibodies against the 4 serotypes of dengue virus in a patient, comprising:

(a) conducting a first administration of a monovalent vaccine comprising a vaccinal virus for a first serotype of dengue fever to the patient, (b) conducting a second administration of a tetravalent vaccine comprising vaccinal viruses for the 4 serotypes of dengue fever to the patient, wherein the vaccinal virus used in the first administration (a) is strain VDV1 or VDV2, and wherein the second administration (b) is performed at least 30 days and not more than 12 months after the first administration (a).

2. The method as claimed in claim 1, wherein the vaccinal viruses used in the tetravalent vaccine are CYD DEN-1,2,3 and 4.

3. The method as claimed in claim 1, wherein the quantity of dengue fever vaccinal viruses of serotypes 1,2,3 and 4 lies within a range from $10^3$ to $10^6$ $DICC_{50}$.

4. The method as claimed in claim 1, wherein the monovalent vaccine comprises $10^4$ $DICC_{50}$ of VDV1 or VDV2 and the tetravalent vaccine comprises about $10^5$ $DICC_{50}$ of CYD DEN-1,2,3 and about $10^3$ $DICC_{50}$ of CYD DEN-4.

5. The method as claimed in claim 1, in which the second administration (b) is performed 30 to 60 days after the first administration (a).

* * * * *